United States Patent [19]

Sealfon

[11] Patent Number: 5,741,227
[45] Date of Patent: Apr. 21, 1998

[54] METHOD OF STERILE PREPARATION OF IV PUMP SYRINGE

[76] Inventor: Andrew I. Sealfon, 24 Carpenter Rd., Chester, N.Y. 10918

[21] Appl. No.: 827,871

[22] Filed: Apr. 11, 1997

[51] Int. Cl.[6] ................................................ A61M 31/00
[52] U.S. Cl. ........................ 604/49; 604/131; 604/151
[58] Field of Search ............................ 604/49, 48, 52, 604/53, 131, 151, 152, 154, 155; 128/DIG. 1, DIG. 12, DIG. 13

[56] References Cited

U.S. PATENT DOCUMENTS 5,423,746  6/1995  Burkett et al. .................... 604/131 X
5,505,709  4/1996  Funderburk et al. .................... 604/155
5,531,697  7/1996  Olsen et al. .............................. 604/131
5,535,746  7/1996  Hoover et al. ........................ 604/152 X

*Primary Examiner*—John D. Yasko
*Attorney, Agent, or Firm*—Myron Amer PC

[57] ABSTRACT

In the method of replacing a filled syringe for an emptied syringe in the same syringe pump, the use of a snap-on disc strategically located on the tubing set of the filled syringe which so facilitates the handling of the tubing set and the syringe pump that contamination during the interconnection of the two is obviated and thus the sterile condition of the syringe is assured, and wherein the disc also holds the filled syringe in place during the urging by the syringe pump of the plunger of the syringe in a power stroke causing the delivery therefrom of medicant to a patient.

2 Claims, 1 Drawing Sheet

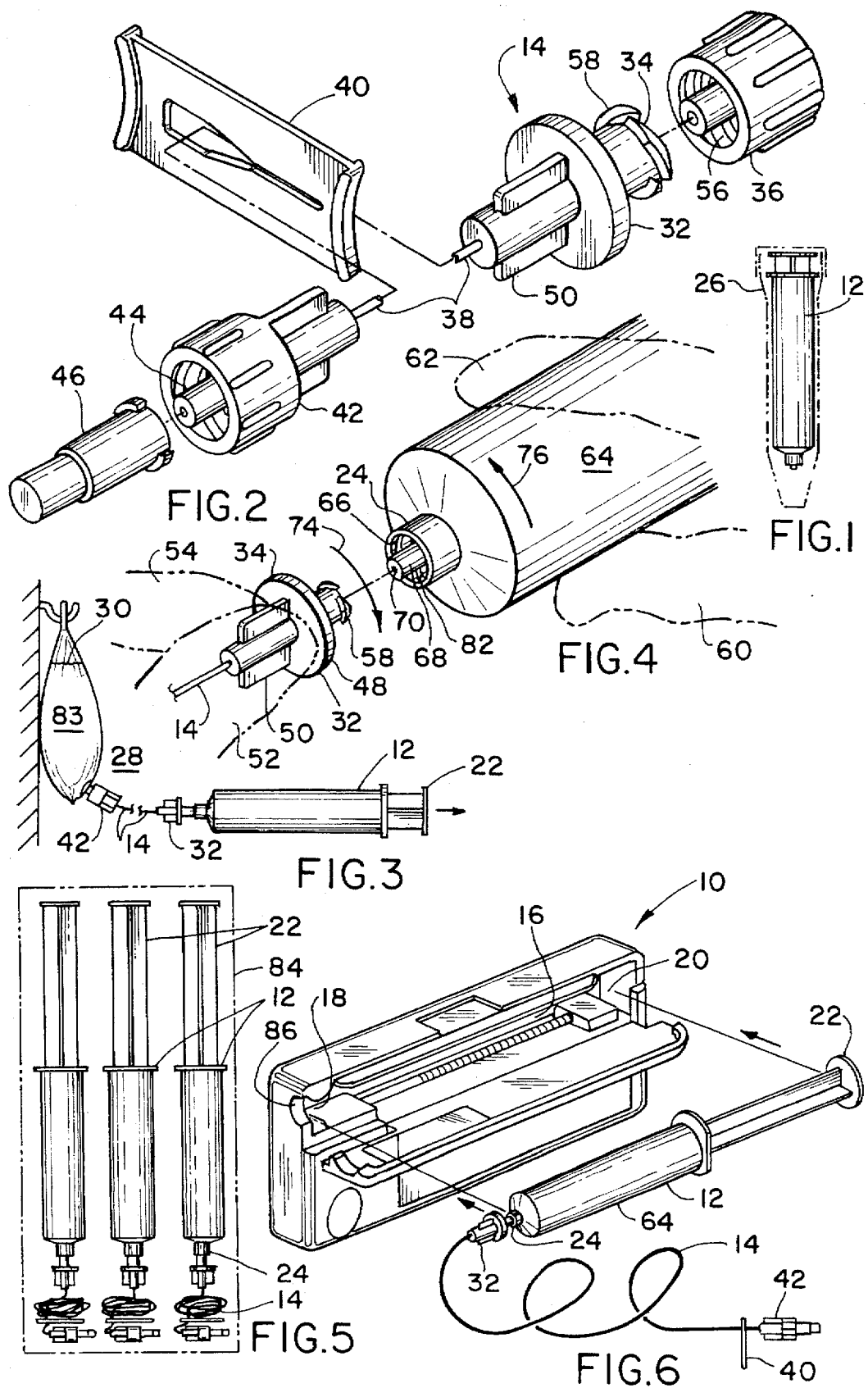

5,741,227

METHOD OF STERILE PREPARATION OF IV PUMP SYRINGE

The present invention relates generally to improvements in the practice of using a single syringe pump for plural syringes, wherein each emptied syringe is discarded and a filled replacement syringe loaded in the just-used syringe pump, with the obvious benefit of obviating the cost of a syringe pump for each syringe, the improvements for this practice being more particularly maintaining the sterile condition of the syringe in the interconnection of the successively used syringes to the syringe pump.

EXAMPLE OF THE PRIOR ART

The economy of using a single syringe pump for successively used syringes is the focus of numerous prior patents, as exemplified by U.S. Pat. No. 5,505,709 issued to Funderburk et al. for "Mated Infusion Pump and Syringe" on Apr. 9, 1996. This patent provides matingly interfitting components to ensure pump use with a compatible and correctly installed syringe.

Another safeguard not provided in this patent or other known patents promoting the practice of using plural syringes with a single syringe pump, and which should be provided, is to ensure that the sterile condition for the replacement syringe is maintained. The sterile condition might be compromised in the interconnection of the replacement syringe to its cooperating tubing set, through which latter component the sterile medicant is delivered to the patient. In a use contemplating a separate syringe pump for each syringe, the maintaining of sterile conditions is state of the art and readily achieved, but this is not the case in the noted use of plural syringes for a single syringe pump.

Broadly, it is an object of the present invention to provide an improved sterile-ensured method using plural syringes with a single syringe pump overcoming the foregoing and other shortcomings of the prior art.

More particularly, it is an object to provide a disk attachment to the tubing set which contributes to maintaining sterile conditions during the handling thereof and the syringe and which also facilitates the use of plural syringes with a single syringe pump, all as will be better understood as the description proceeds.

The description of the invention which follows, together with the accompanying drawings should not be construed as limiting the invention to the example shown and described, because those skilled in the art to which this invention appertains will be able to devise other forms thereof within the ambit of the appended claims.

FIG. 1 is a front elevational view of an empty syringe with an inserted piston plunger in a container in a condition as received at a site of preparation;

FIG. 2 is a perspective exploded view of a tubing set for attachment to a filled syringe of sterile fluid medicant;

FIG. 3 is a side elevational view illustrating the filling of said syringe with sterile fluid medicant under sterile conditions;

FIG. 4 is a partial perspective view, on an enlarged scale, illustrating the interconnection of said tubing set of FIG. 2 to said syringe prior to the said sterile fluid medicant filling thereof of FIG. 3, during which interconnection the sterile condition of the syringe is maintained according to the present invention;

FIG. 5 is an elevational view of plural filled syringes in a shipping container to a site of use; and FIG. 6 is a perspective view of the loading of a said filled syringe of FIG. 5 into a syringe pump at said site of use.

FIG. 6 demonstrates what is already known, namely that, as exemplified by U.S. Pat. No. 5,505,709 issued to Funderburk et al. on Apr. 9, 1996 for "Mated Infusion Pump and Syringe", a single infusion or syringe pump 10 can advantageously be used for plural sterile fluid filled syringes 12, wherein replacement for an emptied syringe with an attached tubing set 14 is adapted to be placed in the clearance 16 between a syringe barrel-engaging means 18 at one end of the syringe pump 10 and a syringe piston plunger-engaging means 20 at an opposite end of the syringe pump 10, and in accordance with the known operating mode of the syringe pump 10, the withdrawn plunger 22 is urged in a power stroke and causes movement of the piston longitudinally of the barrel and consequently forces in exiting flow from the barrel outlet 24 (see FIG. 4) the sterile fluid medicant for delivery through the tubing set 14 to a patient, and thus there is a repeat use for each plural sterile fluid medicant filled syringe of the single syringe pump 10.

A significant adverse tradeoff consequence, however, of the use in sequence of a replacement filled syringe 12 for an emptied syringe, is the possible contamination of the syringe outlet end 24 during interconnection to said end of a tubing set 14. In the referenced patent, for example, the replacement syringe is loaded into the clearance 16 of the syringe pump 10 and the user is required to make the interconnection to said exposed barrel outlet of the inlet of the tubing set. If during this interconnecting procedure the tubing set inlet should contact a surface of the syringe pump 10 other than the barrel outlet 24, contamination is a likely result, and thus the single syringe pump practice for plural syringes of the referenced and all other known similar patents is not in practical use.

In accordance with the present invention, the sterile condition of the syringe 12 and that of the tubing set 14 is maintained during preparation of plural sterile fluid filled syringes 12 for loading into a single syringe pump 10, all as will be readily understood as the description proceeds.

As shown in FIG. 1, an empty syringe 12 is appropriately delivered to a site of preparation in a sealed plastic container 26. There is likewise delivered to the site of preparation, which typically, as shown in FIG. 3, will be understood to be a laboratory of the pharmaceutical manufacturing source of the sterile fluid medicant at which there is a pharmacist, a filling station including a sterile area 28 under a hood and the like, and a source of the sterile fluid medicant 30, a sterile tubing set 14, which tubing set as shown in FIG. 2, consists of an upstream connector 32 with an inlet 34 having an attachable and detachable plug 36, a plastic tube 38 usually 35 inches long extending from the connector 32 through a tubing clamp 40 for connection to a downstream connector 42 having an outlet end 44 also having an attachable and detachable plug 46.

It is at the site of preparation of FIG. 3 that the critical interconnection is made between the barrel outlet 24 and tubing set inlet 34 while maintaining the sterile condition of the syringe 12 and tubing set 14. To this end, there is added to the construction of the tubing set upstream connector 32 a disk 48 in an interposed position between the tubing set per se inlet 34 and a tube-engaging means 50. The upstream connector plug 36 of FIG. 2 is removed and this is facilitated by a pharmacist's left thumb 52 and left index finger 54 engaging the tube-engaging means 50 behind the disk 48 and rotating the plug 36 to unthread internal threads 56 from external threads 59 of the tubing set inlet 34. With the tubing set inlet 34 still in the grasp of the pharmacist's thumb 52 and index finger 54 and thus behind the disk 48, the pharmacist's right thumb 60 and right forefinger 62 grasp the syringe barrel 64 and readily are able to guide the tubing set inlet 34 into a barrel outlet cylindrical compartment 66 and to guide a tubular configuration 68 machined with an exit opening 70 into a cylindrical opening 72 of the tubing set inlet 34 and, during this guiding or aligning procedure, the pharmacist rotates in opposite directions 74 and 76 the tubing set inlet 34 and syringe barrel 64 which threads together the internal threads 82 and external threads 58 of these components, and completes a threaded interconnection of these components. It is significant to note that once the tubing set 14 is connected to the syringe barrel 64 there is no possibility of contamination.

At the site of preparation of FIG. 3 the pharmacist, under sterile conditions prevailing at the station 28, removes the plug 46 from the downstream connector 42 and, in a well understood manner, connects the tubing set outlet 44 to the outlet of a sterile fluid filled bag 83, and withdraws the piston plunger 22 to fill the syringe barrel 64, and afterwards restores the plug 46 to the downstream connector 42 after it is disconnected from the bag 83.

In practice, the noted tubing set may optionally be of a type having an unoccluded or unrestricted flow passage to lessen the time of filling the syringe, and is sometimes replaced by an almost identical tubing set of a type having an intentionally partially restricted flow passage more suitable to provide a slowed-down flow rate to the patient. Whether one or more tubing sets are used, it will be understood that each is prepared for attachment to the syringe outlet end 24 using the disk 48.

As shown in FIG. 5, plural sterile fluid filled syringes 12 are then shipped in a container 84 to a site of use of FIG. 6 at which, as already described, a single syringe pump 10 is loaded with a filled for each emptied syringe, and the sterile-preserving disk 48 during the loading then advantageously facilitates the forcing of the medicant in exiting flow from the syringe by assuming an operative position behind a smaller dimensioned circular configuration 86 than the diameter of the disk 48, thus holding the front end of the syringe barrel 64 stationary while the piston plunger 22 in a power stroke causes the longitudinal movement of the piston within the syringe barrel 64.

While the apparatus for practicing the within inventive method, as well as said method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. A method of preparing for loading under maintained sterile conditions into a syringe pump a syringe of a type having a barrel filled with sterile fluid medicant adapted to be forced in exiting flow from a barrel outlet by a piston urged in a power stroke movement longitudinally of said barrel, said syringe pump for said syringe being of a type having at one end piston barrel-engaging means and in clearance position therefrom at an opposite end a barrel outlet-engaging means, said method comprising the steps of providing a sterile tubing set with inlet and outlet opposite ends for attachment to said barrel outlet preparatory to delivering said fluid medicant from said syringe to a patient, selecting a sterile site maintained under sterile conditions for preparing said syringe for subsequent patient use at a remote site, attaching at said sterile site a disk adjacent said inlet end of said sterile tubing set, gripping with a first hand said barrel and with a second hand removing said plug from said barrel outlet, gripping with said second hand said tubing set from behind said disk so as to obviate contact with said exposed barrel outlet and interconnecting said tubing set inlet end to said barrel outlet, filling at said sterile site said syringe barrel with fluid medicant by withdrawing said piston in a directional movement away from barrel outlet, closing at said sterile site said tubing set outlet with a plug, delivering to said remote site said filled syringe with said attached tubing set, and inserting said interconnected tubing set and syringe in said clearance of said syringe pump with said disk behind said barrel outlet-engaging means and said piston in front of said piston-engaging means, whereby said disk contributes both to maintaining the sterile condition of said syringe during the interconnection of said tubing set thereto and also to holding said syringe barrel stationary during the power stroke movement of said piston longitudinally thereof.

2. A method of preparing for loading under maintained sterile conditions into a syringe pump a syringe of a type having a barrel filled with sterile fluid medicant adapted to be forced in exiting flow from a barrel outlet by a piston urged in a power stroke movement longitudinally of said barrel, said syringe pump for said syringe being of a type having at one end piston barrel-engaging means and in clearance position therefrom at an opposite end a barrel outlet-engaging means, said method comprising the steps of a first step of providing first and second sterile tubing sets each with inlet and outlet opposite ends for attachment to said barrel outlet preparatory to delivering said fluid medicant from said syringe to a patient, a second step of selecting a sterile site maintained under sterile conditions for preparing said syringe for subsequent patient use at a remote site, a third step of attaching at said sterile site a disk adjacent said inlet end of said first sterile tubing set, a fourth step of gripping with a first hand said barrel and with a second hand removing said plug from said barrel outlet, a fifth step of gripping with said second hand said first tubing set from behind said disk so as to obviate contact with said exposed barrel outlet and interconnecting said first tubing set inlet end to said barrel outlet, a sixth step of filling at said sterile site said syringe barrel with fluid medicant by withdrawing said piston in a directional movement away from barrel outlet, a seventh step of replacing said first tubing set with said second tubing set by repeating said third, fourth and fifth steps, an eighth step of closing at said sterile site said second tubing set outlet with a plug, a ninth step of delivering to said remote site said filled syringe with said attached tubing set, and a tenth step of inserting said interconnected tubing set and syringe in said clearance of said syringe pump with said disk behind said barrel outlet-engaging means and said piston in front of said piston-engaging means, whereby said disk contributes both to maintaining the sterile condition of said syringe during the interconnection of said first and second tubing sets thereto and also to holding said syringe barrel stationary during the power stroke movement of said piston longitudinally thereof.

\* \* \* \* \*